United States Patent [19]
Johnson

[11] Patent Number: 6,027,469
[45] Date of Patent: Feb. 22, 2000

[54] DISINFECTING SYSTEM FOR HEMODIALYSIS APPARATUS

[76] Inventor: Lee D. Johnson, 9409 Randall Dr. NW., Gig Harbor, Wash. 98332

[21] Appl. No.: 09/205,156

[22] Filed: Dec. 3, 1998

[51] Int. Cl.[7] .......................... A61M 37/00; B01D 11/00
[52] U.S. Cl. ................................ 604/4; 210/645; 210/646
[58] Field of Search .................... 604/4–6, 500; 422/44; 210/645, 646

[56] References Cited

U.S. PATENT DOCUMENTS

| | | | |
|---|---|---|---|
| 3,911,115 | 10/1975 | Hadhanyi | 424/180 |
| 5,437,858 | 8/1995 | Hungerbach et al. | 424/53 |
| 5,603,902 | 2/1997 | Maltais et al. | 422/103 |
| 5,759,489 | 6/1998 | Miura et al. | 422/28 |
| 5,776,091 | 7/1998 | Brugger et al. | 604/4 |
| 5,895,578 | 4/1999 | Simard et al. | 210/636 |
| 5,945,032 | 8/1999 | Breitenbach et al. | 252/186.29 |

*Primary Examiner*—Corrine McDermott
*Assistant Examiner*—Cheryl S. Huseman
*Attorney, Agent, or Firm*—Seed and Berry LLP

[57] ABSTRACT

A colloidal silver solution is introduced as a disinfectant to the blood and dialysate sides of a hemodialysis system at the conclusion of a dialysis session and is not flushed from the system until another dialysis is to be performed.

18 Claims, 1 Drawing Sheet

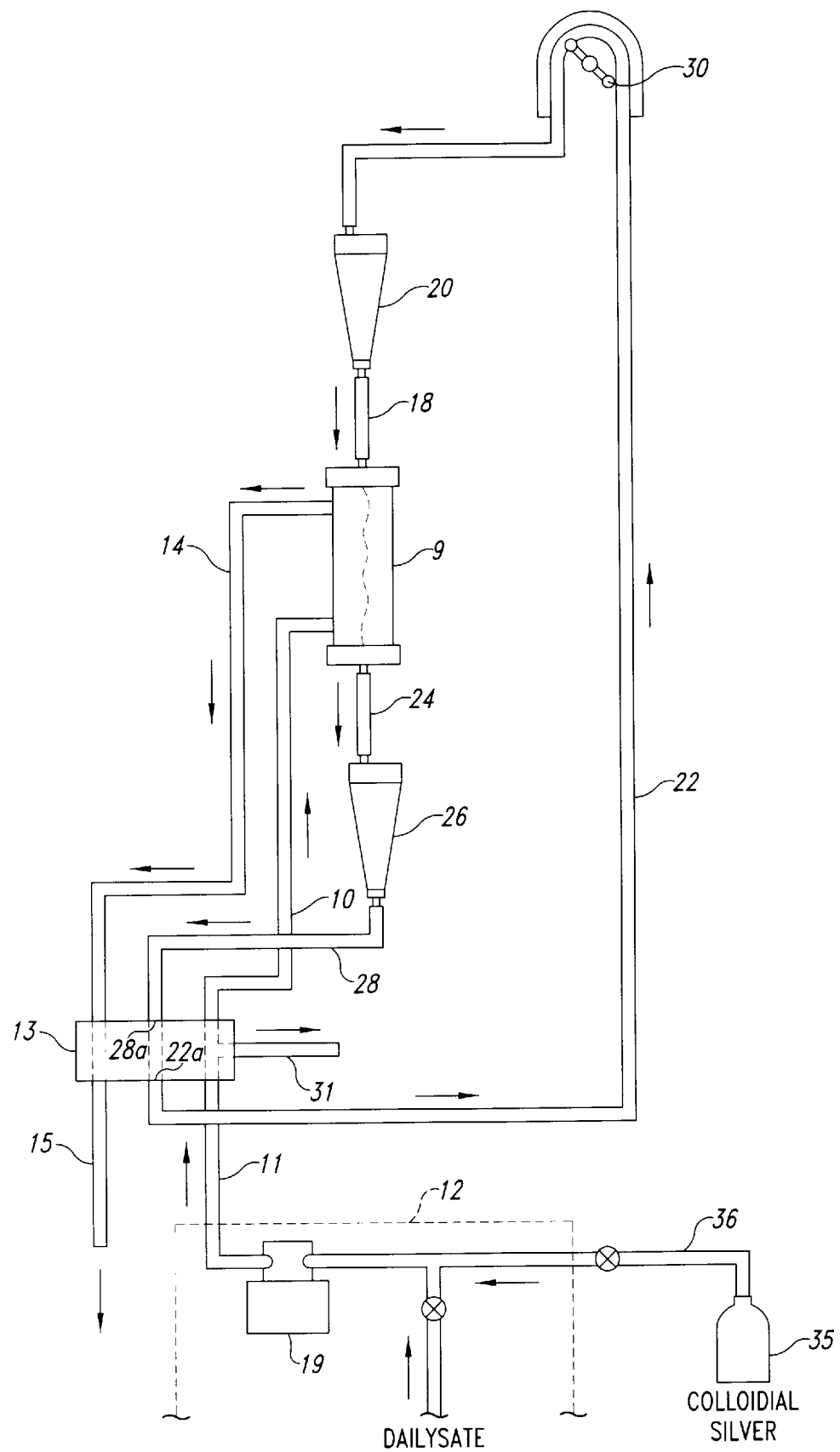

DISINFECTING SYSTEM FOR HEMODIALYSIS APPARATUS

TECHNICAL FIELD

The present invention relates to the reuse of components in a hemodialysis system, and particularly, the manner of disinfecting them.

BACKGROUND OF THE INVENTION

The reuse of disposable artificial kidneys has grown greatly in the United States to the extent that reuse is reported to be practiced by more than 75% of all hemodialysis facilities. Reuse requires a cleaning and disinfecting program between uses for the dialyzer, blood and dialysate tubing sets, and related apparatus that guarantees bacteriological safety, the avoidance of contamination by the chemicals used in the cleaning and disinfecting process, and maintenance of the transfer efficiency of the dialyzer membrane. Economic concerns dictate that the reuse cycle be expedited and involve as little expense as possible.

In the past, various reuse procedures and apparatus have been developed to substantially automate cleaning, rinsing and sterilization cycles. U.S. Pat. No. 4,695,385 discloses a reuse system which has enjoyed some success. In this system as normally practiced, sterilization is accomplished by use of a formaldehyde solution, and it is essential that the blood, tubing and blood side of the dialyzer be absolutely free of formaldehyde before reuse since formaldehyde is extremely toxic if permitted to enter a patient's blood stream.

In U.S. Pat. No. 4,695,385, the blood tubing is isolated during the disinfecting cycle with the blood side of the dialyzer in a closed loop filled with the formaldehyde solution. This status is maintained during idle periods of the dialysis machine. To remove the formaldehyde from the system in preparation for another patient, the blood pump is started to circulate the formaldehyde solution in the closed loop, and the dialysate pump is started to circulate dialysate through the dialysate side of the dialyzer. As a result, molecular transfer of the formaldehyde across the dialyzer membrane occurs and the transferred formaldehyde is disposed of with the circulating dialysate. The formaldehyde solution in the blood tubing can be provided with a colored dye indicator so that there can be visual confirmation that the formaldehyde has been substantially removed. Then a chemical test is performed to verify that no disinfectant residue remains in the dialysis system.

A survey in 1996 indicated that about 90% of dialyzer centers used formaldehyde or Renalin as a dialyzer disinfectant. Renalin (Renal Systems, Minneapolis, Minn.) is a hydrogen peroxide-paracetic acid based product. At least one major manufacturer of hemodialysis machines advises that such peracetic acid products should be rinsed out after acting for 20 minutes and warns that they should not be left in the machine overnight because damage to internal components may occur. Also, some studies have indicated increased health risk concerns when peracetic acid is used in reprocessing dialyzers. Thus, heretofore, formaldehyde has been considered preferable for use as a dialyzer disinfectant for the blood circuit components, particularly when the dialysis machine may be idle for several hours, and therefore, preferably should have its blood circuit components exposed to disinfectant while idle to avoid the possibility of bacterial growth.

From the foregoing discussion it is seen that although it has been recognized that ideally the disinfecting agent for disinfecting a hemodyalisis system for reuse should be a chemically pure, non-toxic substance that can be easily removed from the dialyzer so as to minimize the risk to the patient from exposure to trace amounts, heretofore, not only was a suitable non-toxic disinfecting substance never found, but it has been considered that disinfectant removal from the blood side of the system requires that the disinfecting solution be dialyzed for removal of the disinfectant.

SUMMARY OF THE INVENTION

Accordingly, it is apparent that there has been a significant need for an improved method for sterilization of the dialyzer and associated blood and dialysate exposed tubing and components in a hemodialysis machine when they are to be reused. I have found that this need can be filled by properly using colloidal silver as a disinfectant, preferably at a concentration of about 3 ppm. This disinfectant is circulated to fill the dialyzer and associated sets of dialysate and blood tubing and related apparatus after they have been rinsed following a dialysis treatment. The disinfectant is preferably left in place until shortly before another treatment is scheduled. Then the disinfectant may be flushed from the dialysis system with sterile water; no dialysis of the disinfectant is required for removal. However, even this water flushing is not essential because colloidal silver is not toxic. Hence, at the start of dialysis, when the blood is initially being pumped from the patient through the blood tubing and blood side of the dialyzer, the blood will flush the colloidal silver solution out of the tubing and dialyzer through the venous end of the tubing before the venous end is connected for the patient following appearance of the patient's blood at the venous end. The colloidal silver solution in the dialysate circuit will be flushed to drain by the circulating dialysate. It is of no concern if colloidal silver residue remains in the blood circuit and is gathered up by the patient's circulating blood because colloidal silver is not toxic, particularly in the concentration used.

BRIEF DESCRIPTION OF THE DRAWINGS

FIG. 1 is a schematic of a typical hemodialysis system to which the present invention may be applied.

DETAILED DESCRIPTION OF THE INVENTION

Referring to FIG. 1, there is illustrated a hemodyalisis system having a dialyzer 9 containing a suitable membrane separating a blood side from a dialysate side. The latter is connected to a dialysate tubing set including an input line 10 connected to a supply line 11 from the dialysis machine 12 via a valve block 13, and a discharge line 14 leading to a drain line 15 via the valve block 13. The blood side of the dialyzer 9 has an inlet connected by a blood tube 18 to an arterial drip chamber 20 feeding from an arterial blood tube 22, and has an outlet feeding by a blood tube 24 to a venous drip chamber 26. This chamber discharges to a venous line 28. During dialysis the ends 22a and 28a of the blood tubes 22, 28 of the blood tube set are connected to the patient. A blood pump 30 operates to move blood from the patient to the blood side of the dialyzer where the toxins in the blood are transferred via the dialyzer membrane to the circulating dialysate on the other side of the membrane. The dialysate is mixed and pumped by a suitable pump 19 from the dialysis machine 12 to the dialyzer through supply line 11, valve block 13, and input line 10. After circulating through the dialyzer the then used dialysate is dumped through the discharge tubing 14, valve block 13, and a drain line 15.

After dialysis is completed, the arterial blood tube 22 is disconnected from the patient and it and the remaining blood side of the system are emptied of blood, preferably by pumping a disinfecting colloidal silver solution through the blood tube 22 until substantially all of the blood in the blood side is returned to the patient through the venous line 28. Then the venous line 28 is disconnected from the patient and circulation of the colloidal silver solution may be continued to purge the blood side of the system from remaining blood. The colloidal silver solution may be stored in a vessel 35 connected by a suction tube 36 to the suction side of the pump 19 so that the colloidal silver solution may be pumped through the line 11 to the valve block 13 where a suitable valve directs the flow to a branch 31 or input line 11 to the dialyzer 9. The arterial tubing 22 is connected to the branch 31 when the colloidal silver solution is to be circulated through the blood side of the system as at the end of a dialysis session to return as much of the patient's blood as feasible to the patient. When the blood side is full of the colloidal silver solution, the pumping may be stopped and the valving in the valve block 13 is set so that the arterial and venous lines 27, 28 are interconnected to make the blood side of the system a closed loop filled with the colloidal silver solution to maintain the blood side of the dialysis system in a disinfected condition until the start of the next dialysis session.

In the meantime, the dialysate side of the system can be flushed with water and then filled with colloidal silver solution in like manner as the blood side. When dialysis is to be again performed, dialysate is circulated through the dialysate side of the system and this adequately flushes out the colloidal silver solution. Likewise, the colloidal silver solution filling the blood side of the system can be removed by water flushing the blood lines and blood side of the dialyzer. However, since colloidal silver solution is not toxic, it can be adequately removed from the blood side by connecting the arterial tubing 22 to the patient, starting the blood pump 30, and commencing dialysis without the venous line 28 being connected to the patient. As the pumped blood travels through the blood side of the system it flushes out the colloidal silver solution through the outer end 28a of the venous line. When blood appears at this end 28a, the venous line is connected to the patient.

The preferred concentration of colloidal silver in sterile water for use according to the present invention is 3 ppm±10%. Greater concentrations can be used but there is no significant increase in disinfecting effectiveness, and there is the disadvantage of being more costly. In fact, concentrations above about 5 ppm do not give as good results for the practice of the present invention as concentrations of about 3 ppm.

A suitable colloidal silver solution can be produced in a batch procedure by suspending two substantially pure silver electrodes, as anode and cathode, about six inches apart in a large non-metallic container of pure water (preferably distilled) and subjecting the electrodes to a relatively high alternating current voltage, as for example, 440 volts. This procedure is continued until sufficient silver particles have sloughed into the water to achieve the desired concentration, and namely, about 3 ppm in the present instance. These silver particles are very minute, typically in the range of about 0.005 to 0.015 microns, and normally have the same polarity. Hence, the particles remain suspended in the water in a colloidal state.

From the foregoing it will be appreciated that, although the blood side of the system may include more or less components than discussed, the described sterilization procedure is equally applicable. Accordingly, the invention is not limited except as by the appended claims.

I claim:

1. A method for disinfecting those components of a hemodialysis system through which blood is circulated during dialysis of a patient during a first dialysis session and which are to be reused during the next dialysis session, said method comprising:

filling said components after said first session with a colloidal silver solution having a colloidal silver concentration about 3 ppm, and maintaining such filled condition until the start of said next dialysis session.

2. A method according to claim 1 in which said colloidal silver solution present in said components at the start of said next dialysis session is purged from said components by circulating blood therethrough from the patient undergoing said next session.

3. A method according to claim 1 in which said colloidal silver solution present in said components at the start of said next dialysis session is purged from said components by circulating pure water through said components followed by circulating blood therethrough from the patient undergoing said next session.

4. A method according to claim 1 in which components of said system through which dialysate is circulated during such dialysis of a patient, are flushed with a colloidal silver solution after said first dialysis session.

5. A method according to claim 1 in which components of said system through which dialysate is circulated during such dialysis of a patient, are also filled after said first session with a colloidal silver solution and are maintained in such filled condition until the start of said next dialysis session.

6. A method according to claim 1 in which said colloidal silver solution is produced by passing a high voltage alternating current between two silver electrodes suspended in pure water.

7. A method for disinfecting blood contaminated components in a hemodialysis system following a dialysis session in which a patient's blood was circulated through said components, said method comprising:

flushing the blood contaminated components with a disinfecting solution containing colloidal silver;

then keeping said components filled with said solution during an inactive period before another dialysis session; and removing said solution from said components at the start of the next dialysis session.

8. A method according to claim 7 in which said components include blood tubing and the blood side of a dialyzer.

9. A method according to claim 7 in which said disinfecting solution consists of colloidal silver suspended in pure water, the concentration of colloidal silver being between 2.7 and about 5 ppm.

10. A method for disinfecting blood contaminated components in a hemodialysis system following a dialysis session in which a patient's blood was circulated through said components, said method comprising:

flushing blood of said patient in said components from said components back to said patient at the close of said dialysis session by circulating a disinfecting solution through said components, said solution consisting of colloidal silver suspended in pure water;

keeping said components filled with said solution during an inactive period between said close of the dialysis session and the start of the next dialysis session; and purging said solution from said components at the start of said next session with blood circulating from the patient undergoing said next session.

11. A method according to claim 10 in which the concentration of colloidal silver in said disinfecting solution is about 3 ppm.

12. A method for disinfecting a hemodialysis system following a dialysis session including as components a blood tubing set, a dialysate tubing set, and a dialyzer having a dialysate side in communication with said dialysate tubing set and having a blood side in communication with said blood tubing set, said system normally operating during dialysis by blood being circulated from a patient through the blood side of the dialyzer to be dialyzed and back to the patient via the blood tubing set, and by dialysate being supplied to the dialysate side of the dialyzer and discharged therefrom via the dialysate tubing set, said method including flushing said dialysate tubing set and said dialysate side with a disinfectant, flushing said blood tubing set and said blood side with a disinfecting solution containing a disinfecting concentration of colloidal silver in sterile water, then keeping said blood tubing set and said blood side filled with said solution during an inactive storage period in which said solution is not circulating, and, at the conclusion of said storage period, purging disinfectant from, and circulating dialysate through, said dialysate tubing set and dialysate side of the dialyzer, and purging said solution from, and circulating blood from a patient through, said blood tubing set and blood side of the dialyzer in a manner dumping said solution and returning the circulating blood to the patient.

13. A method according to claim 12 in which said disinfecting concentration of colloidal silver is about 3 ppm.

14. A method according to claim 12 in which the colloidal silver solution is produced by passing high voltage alternating current between two silver electrodes suspended in sterile water.

15. A method according to claim 12 in which said disinfectant in said dialysate tubing set and the dialysate side of the dialyzer also comprises a disinfecting concentration of colloidal silver in sterile water.

16. A method according to claim 12 in which said disinfecting solution is purged from said blood tubing set and blood side of the dialyzer by said circulating blood from the patient.

17. A method according to claim 15 in which said disinfectant in said dialysate tubing set and dialysate side of the dialyzer is purged therefrom by said circulating dialysate.

18. A method according to claim 12 in which said disinfecting concentration of colloidal silver is between 2.7 and about 5 ppm.

* * * * *